United States Patent
Siebert et al.

(10) Patent No.: US 7,018,519 B1
(45) Date of Patent: *Mar. 28, 2006

(54) MULTICAPILLARY ELECTROPHORESIS SYSTEMS

(76) Inventors: Rainer Siebert, 6, rue du Socteur Vaillant, 78340 Les Clayes-Sous-Bois (FR); Samuele Bottani, 21 rue du Depart, 75014 Paris (FR); Hans Rebscher, Dammstra. 7, D—68169, Mannheim (DE); Luc Valentin, 36. rue Gometz, 91440 Bures (FR); Gilbert Gauguet, 18, allee de la Croix Saint Pierre, 91191 Gif sur Yvette (FR)

( * ) Notice: Subject to any disclaimer, the term of this patent is extended or adjusted under 35 U.S.C. 154(b) by 210 days.

This patent is subject to a terminal disclaimer.

(21) Appl. No.: 09/632,573

(22) Filed: Aug. 4, 2000

Related U.S. Application Data

(63) Continuation-in-part of application No. 09/402,219, filed as application No. PCT/FR99/00184 on Jan. 29, 1999, now Pat. No. 6,613,212.

(30) Foreign Application Priority Data

Jan. 30, 1998 (FR) .................................. 98 01091

(51) Int. Cl.
*G01N 27/453* (2006.01)
(52) U.S. Cl. ...................................... 204/603; 204/601
(58) Field of Classification Search ................ 204/603, 204/452, 601, 451; 356/344
See application file for complete search history.

(56) References Cited

U.S. PATENT DOCUMENTS

| | | | | | |
|---|---|---|---|---|---|
| 5,194,915 | A | * | 3/1993 | Gilby | .......................... 356/318 |
| 5,240,585 | A | * | 8/1993 | Young et al. | ................ 204/601 |
| 5,290,587 | A | * | 3/1994 | Young et al. | ................ 427/122 |
| 5,567,294 | A | * | 10/1996 | Dovichi et al. | .............. 204/603 |
| 6,054,032 | A | * | 4/2000 | Haddad et al. | .............. 204/451 |
| 6,613,212 | B1 | * | 9/2003 | Siebert et al. | .............. 204/603 |

FOREIGN PATENT DOCUMENTS

| | | | |
|---|---|---|---|
| EP | 723149 | * | 7/1996 |
| JP | 03092756 A | * | 4/1991 |
| JP | 10019846 A | * | 1/1998 |

OTHER PUBLICATIONS

Derwent abstract of Hitachi (JP 03092756 A).*

* cited by examiner

*Primary Examiner*—Alex Noguerola
(74) *Attorney, Agent, or Firm*—Blakely Sokoloff Taylor & Zafman

(57) ABSTRACT

A multicapillary electrophoresis system includes juxtaposed capillaries, at least one source configured for the emission of a light beam intended to excite molecules lying in its path and inside the capillaries and detects the fluorescence of the molecules excited by the light beam. Light that emerges at the exit of the capillaries and that propagates along the direction in that the capillaries extend is detected. The resolution for detection is high enough to distinguish light that emerges at the exit of each of the capillaries. A first liquid is located outside of the capillaries. A second liquid is located inside of the capillaries. The first liquid has a first refractive that is equal to or greater than the refractive index of the second liquid. A mirror is facing the source on the side of the capillaries which is opposed to the source.

33 Claims, 17 Drawing Sheets

FIG_1

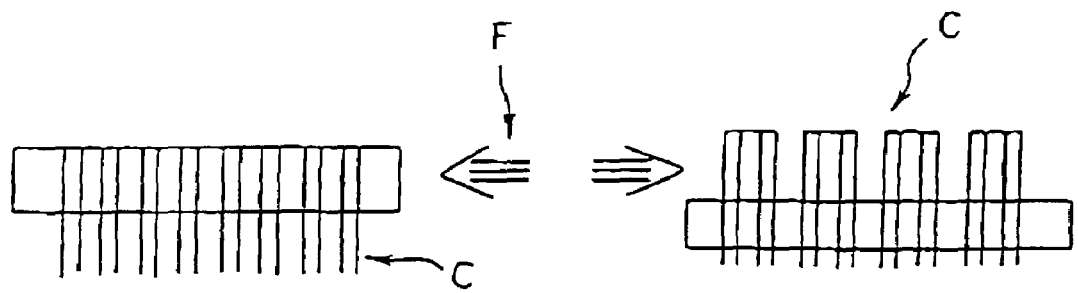
FIG_6a  FIG_6b
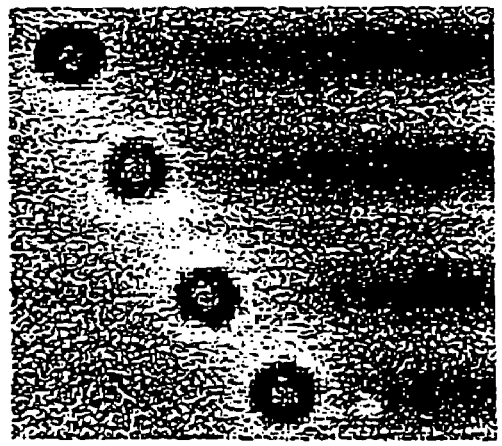 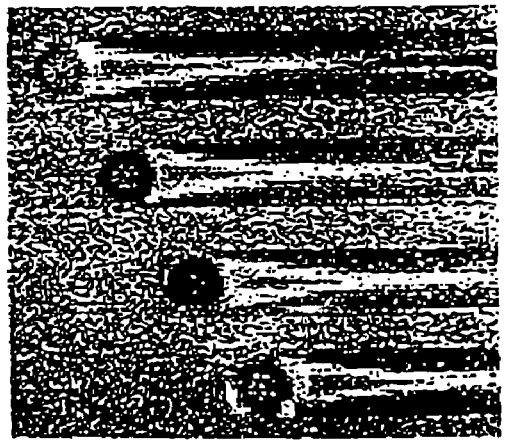
FIG_7a  FIG_7b

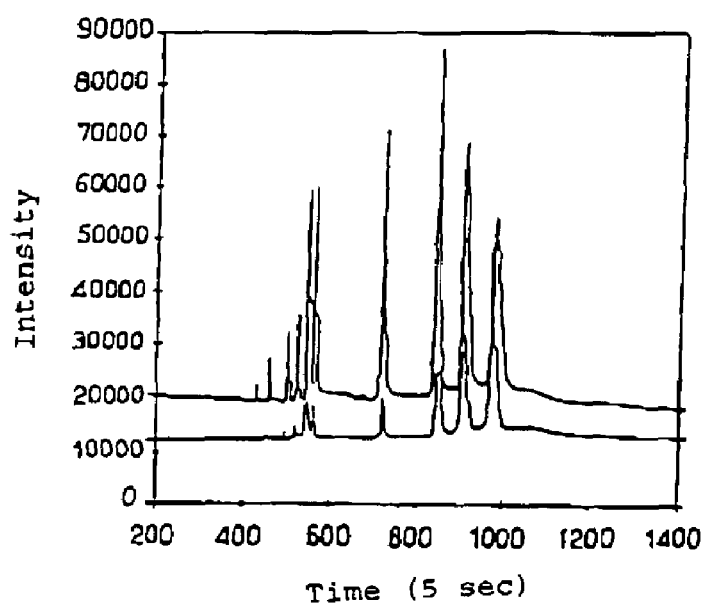
FIG_12a

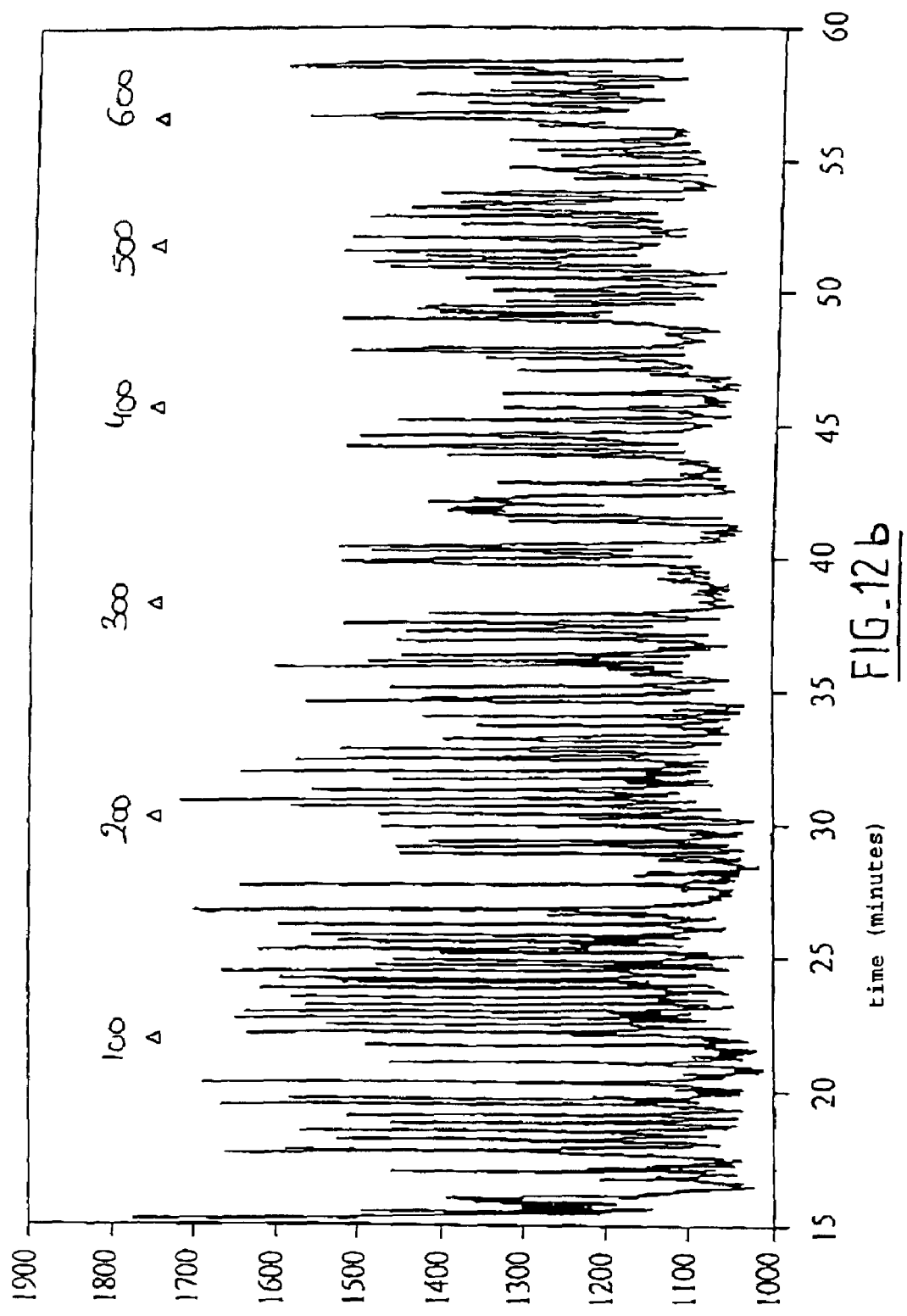
FIG_12b ent application Ser. No. 09/402,219 filed on Feb. 7, 2000, now U.S. Pat. No. 6,613,212, which claims priority from International application Serial No. PCT/FR99/00184 filed on Jan. 29, 1999.

MULTICAPILLARY ELECTROPHORESIS SYSTEMS

This application is a continuation-in-part of U.S. patent application Ser. No. 09/402,219 filed on Feb. 7, 2000, now U.S. Pat. No. 6,613,212, which claims priority from International application Serial No. PCT/FR99/00184 filed on Jan. 29, 1999.

The present invention relates to multicapillary electrophoresis systems.

It is known that conventional gel electrophoresis techniques, in which various samples are injected along a plurality of tracks defined in a gel placed between two plates, are not satisfactory, given that, on the one hand, they require a number of manual operations and, on the other hand, they do not allow very high migration velocities and therefore very high treatment throughputs.

However, the major sequencing and genotyping programs require a very high rate of separation and identification of DNA molecules.

Moreover, electrophoresis techniques are known which use, for the migration, a capillary filled with gel or with another separating matrix having the advantage of being particularly handleable, easy to load and which allow substantially automatic operation, with higher separation rates than in electrophoresis using gel slabs by virtue of a high electric field that can be applied.

However, the use of a single capillary does not make it possible to achieve the same rates as those allowed by electrophoresis techniques using slabs which possess many parallel tracks, even if nevertheless the electric fields that can be applied to a capillary, and therefore the migration velocities obtained, are high.

This is why systems called multicapillary systems comprising a linear array of several juxtaposed capillaries have also been proposed.

In particular, multicapillary electrophoresis systems are known in which the laser beam for exciting the molecules is sent into the capillaries through their walls, along an axis in the plane of the linear array, perpendicular to the direction along which the capillaries extend, the fluorescence of the molecules being observed by receiving means having an optical axis perpendicular to the plane of the linear array of capillaries.

In this regard, reference may be made, for example, to the publication: "A Capillary Array Gel Electrophoresis System Using Multiple Laser Focusing For DNA Sequencing"—T. Anazawa, S. Takahashi and H. Kambara, Anal. Chem., Vol. 68, No. 15, Aug. 1, 1996, pp. 2699–2704.

However, such a technique is not very satisfactory on account of the detection noise resulting from the interaction of the excitation light and the fluorescence from the walls of the capillary. Furthermore, the laser beam loses intensity as it passes through the capillaries, so that the molecules which are located in the capillaries furthest from the laser source are less excited than those moving in the first capillaries.

Because of these major drawbacks, the systems of the type of those described in the publication: "Analysis of Nucleic Acids by Capillary Electrophoresis" by C. Heller, pp. 236 to 254, Editions Vieweg, 1997, or else in the patents and patent applications U.S. Pat. No. 5,567,294 or EP-723,149, are generally preferred to multicapillary electrophoresis systems in which the laser beam for exciting the molecules is sent into the latter through the walls of the capillaries.

In the systems described in that publication or those patents, the capillaries are held one with respect to the other in a glass cuvette along which said capillaries extend. The molecules which travel along the capillaries are excited after having exited said capillaries by a beam of laser radiation which is sent, just at the exit of the linear array, in the plane of said linear array and perpendicular to the direction along which the capillaries extend.

The fluorescence of the molecules excited by this radiation is detected, for example, by means of a CCD camera which is oriented with an axis perpendicular to the plane of the linear array of capillaries or else with an axis parallel to the capillaries.

However, such a system requires means to be provided, such as laminar flow means or guiding elements, which prevent the molecules from diverging too significantly at the exit of the various capillaries. To do this, the cuvette requires a high-precision mechanical construction in glass. In particular, the device will have to provide a very uniform flow and avoid any gas bubbles or dust disturbing the flow.

Furthermore, this technique requires the use of different materials—at least as regards the viscosity—for the capillaries and the cuvette, which have different functions, one serving for separating the molecules and the other for channeling the flows. It therefore becomes necessary to use large volumes of solutions to produce the flow.

As will have been understood, such a technique has the drawback of being particularly expensive.

One aim of the invention is therefore to propose a multicapillary electrophoresis system which, for chemical and pharmaceutical applications, is robust, inexpensive, reliable and easy to use and whose performance allows high-throughput sequencing and genotyping.

For this purpose, the invention proposes a multicapillary electrophoresis system comprising a plurality of juxtaposed capillaries, at least one source for the emission of a beam intended to excite molecules lying in its path and inside the capillaries and means for detecting the fluorescence of the molecules excited by said beam.

In order to alleviate the drawbacks which, in the known systems in the prior art, caused those skilled in the art to move away from this type of system, the invention proposes to arrange the detection means so as to detect the light which emerges at the exit of said capillaries and which propagates along the direction in which said capillaries extend, as well as to use detection means having a high enough resolution to distinguish the light which emerges at the exit of the capillaries from that coming from the walls of the latter and/or from the medium which surrounds them.

Such a structure makes it possible to detect molecules inside the capillaries while considerably reducing the detection noise.

This system is advantageously completed by the following various advantageous characteristics taken by themselves or in any of their technically possible combinations:

it includes a matrix of capillaries;

it includes means, such as microlenses, for producing multiple focusing on a linear array of capillaries;

one linear array of capillaries produces multiple focusing at the entry of the following linear array;

the excitation beam is of elongate cross section and strikes several superposed capillaries simultaneously;

the space between the capillaries is filled, at least along the path of the excitation beam, by a material whose refractive index is chosen so that the excitation beam does not diverge after having traveled along a capillary;

said material is transparent and non-fluorescent;

it includes means for applying pressure in the detection cuvette, which pressure allows the capillaries to be filled with the separating matrix;

it includes dispersion means for spatially separating the various fluorescence wavelengths;

the detection means provide a complete image of the light exiting the capillaries;

the detection means comprise detection means of the charge-coupled device (CCD) type, as well as focusing means;

the detection means comprise detection means of the charge-coupled device (CCD) type, as well as a fiber bundle interposed between the exits of the capillaries and the detection means of the charge-coupled device type.

Further features and advantages of the invention will also emerge from the description. This description is purely illustrative and non-limiting. It must be read with regard to the appended drawings in which.

Figure 1:
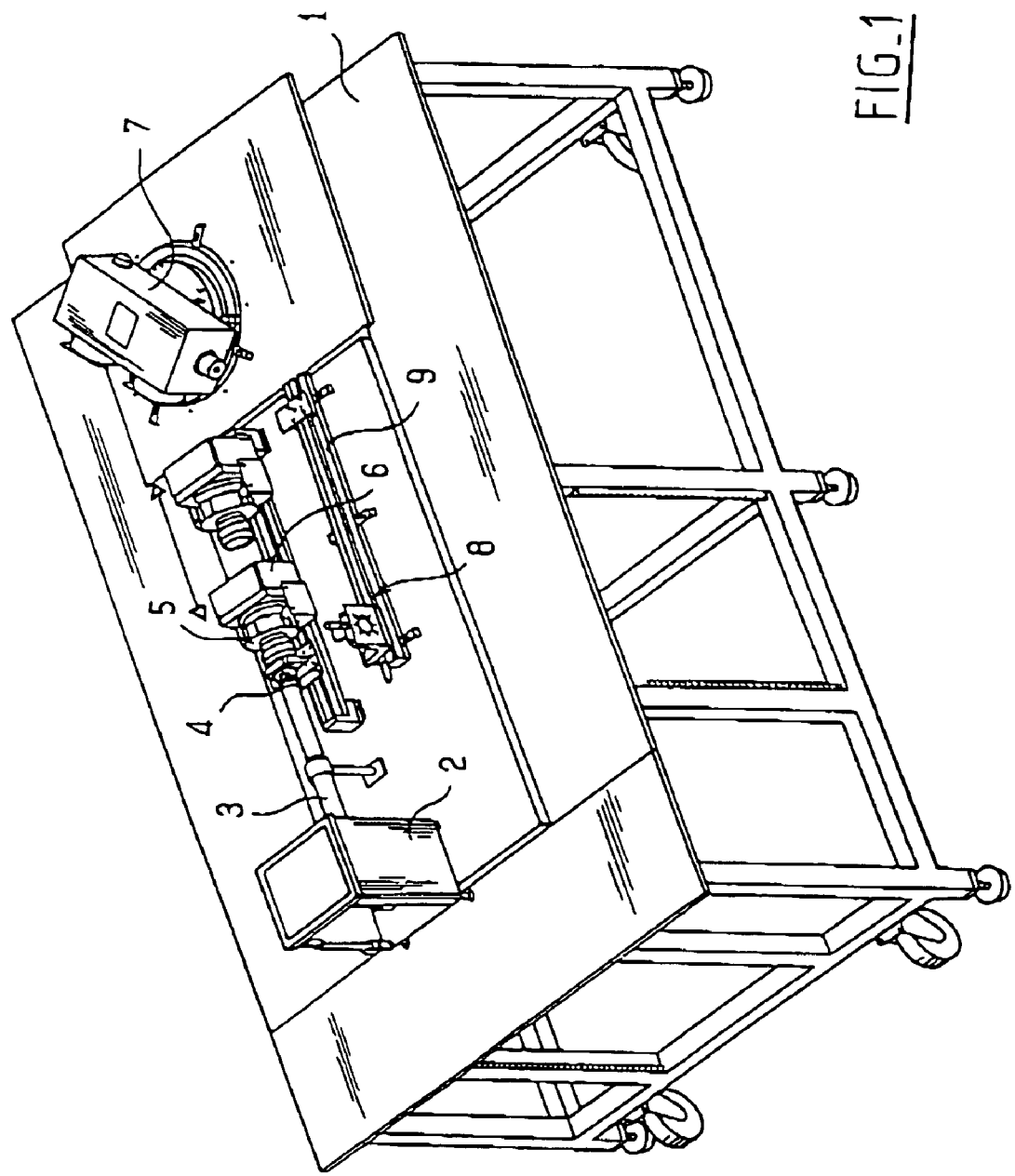
FIG. 1 is a schematic perspective representation of a system in accordance with one possible embodiment of the invention.
Figure 3A:
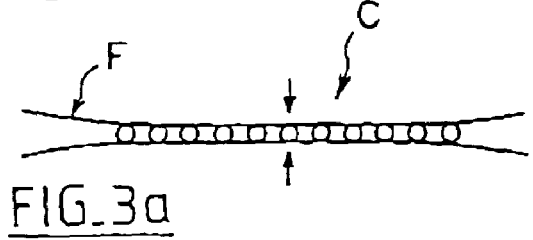
Figure 3B:
Figure 4A:
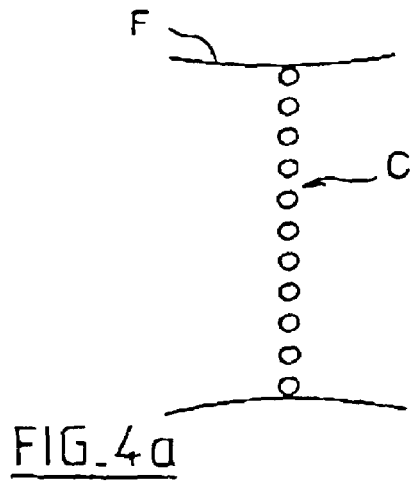
Figure 4B:
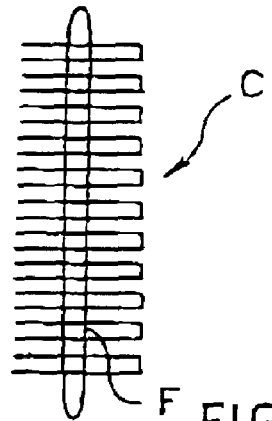
Figure 5:
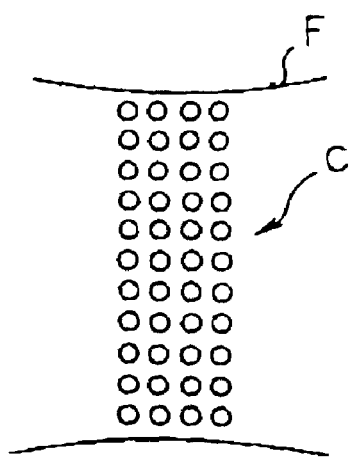
Figure 8:
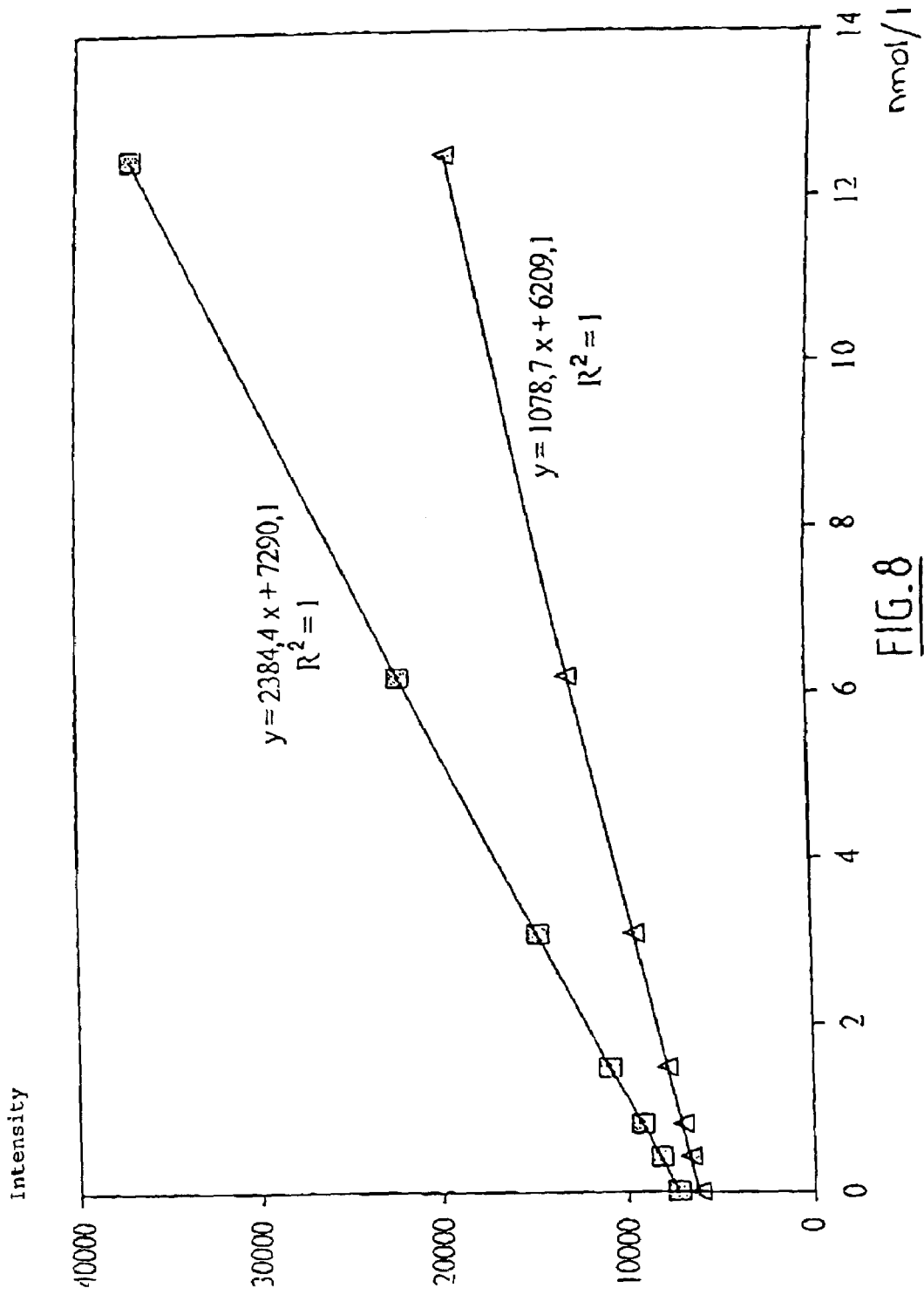
Figure 9:
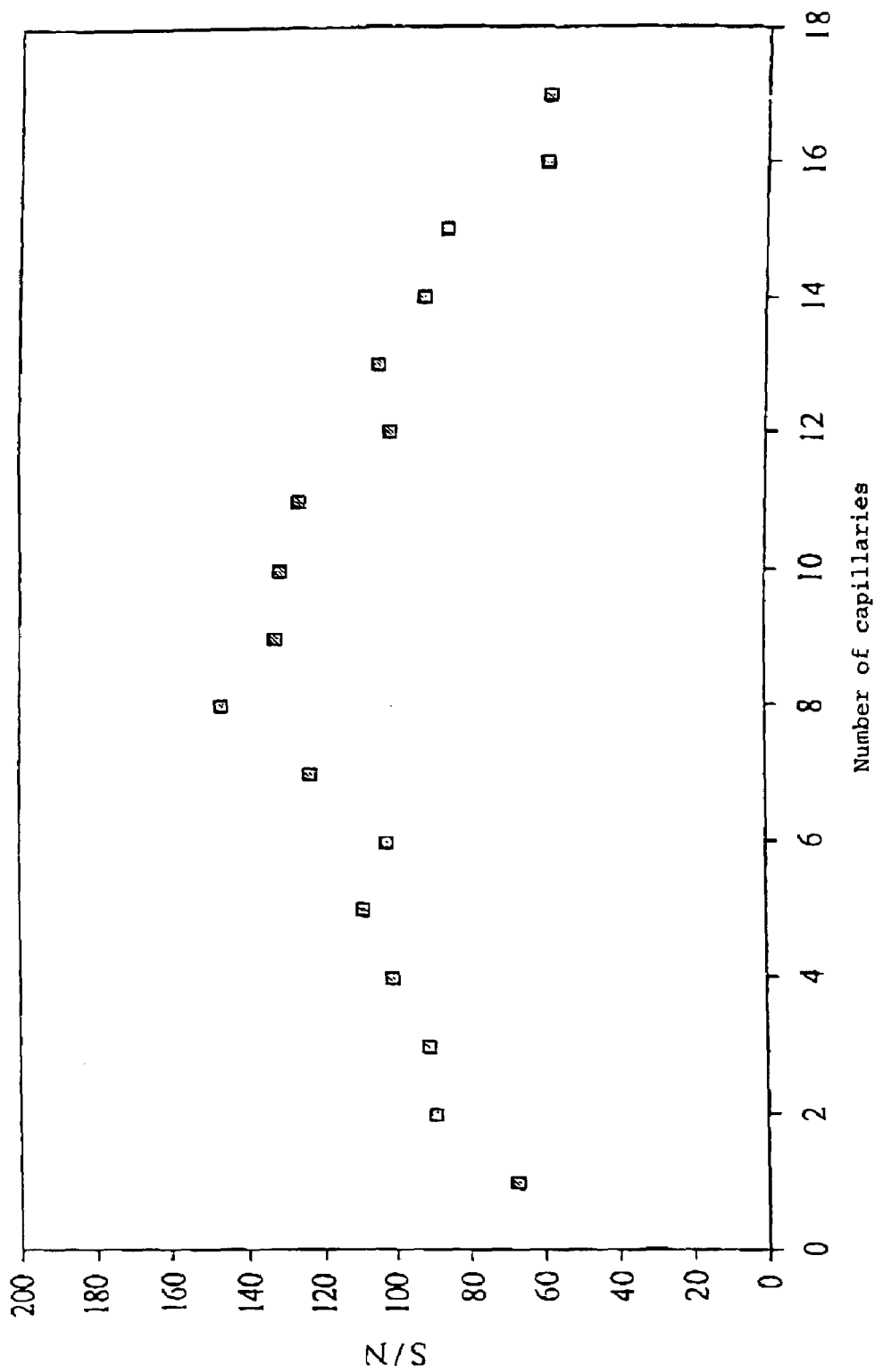
Figure 10:
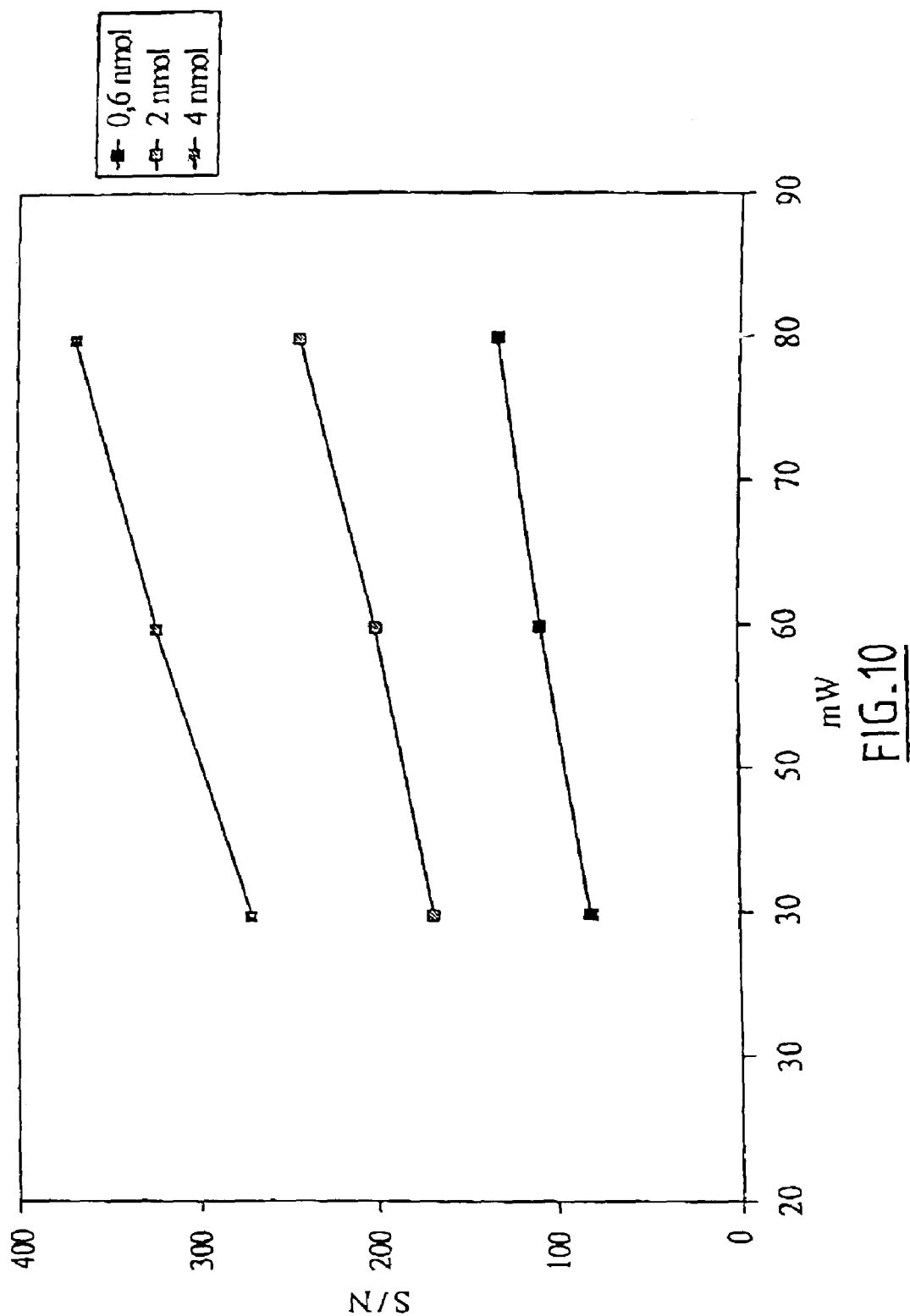
Figure 11:
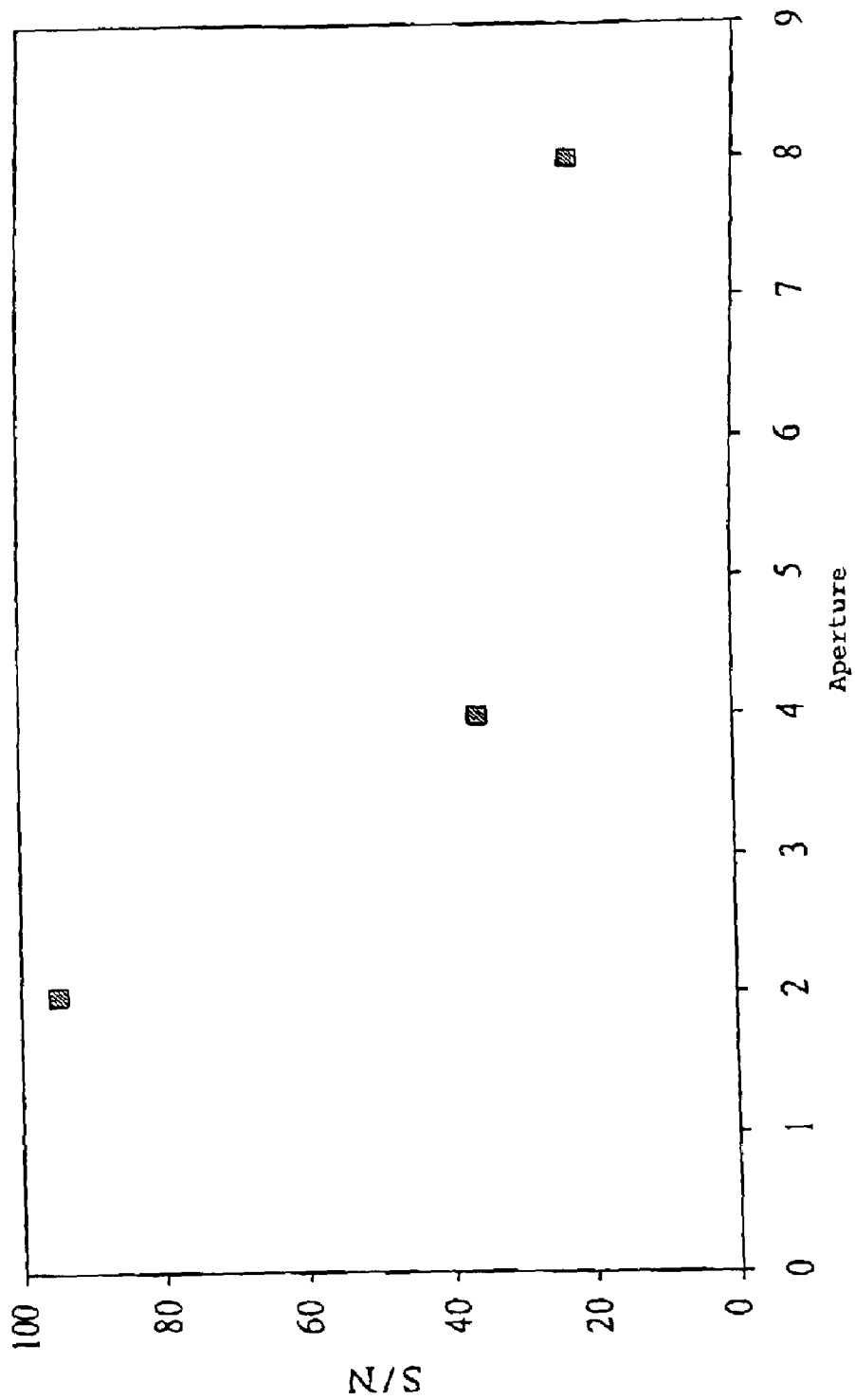
Figure 13:
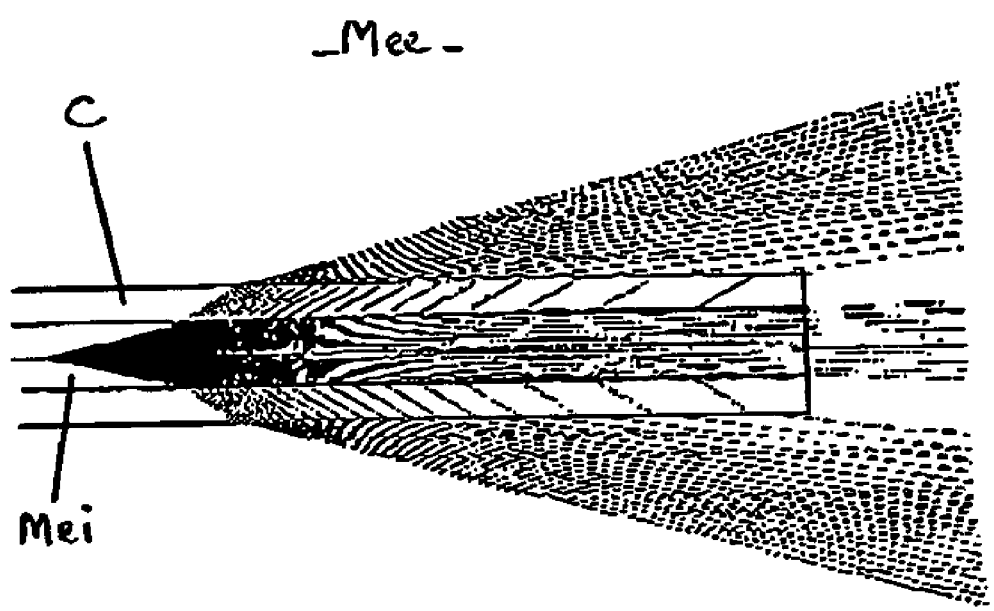

FIGS. 3*a* and 3*b* illustrate the use of an excitation beam of circular cross section;

FIGS. 4*a* and 4*b* illustrate the use of a beam of elliptical cross section;

FIG. 5 illustrates the use of a matrix of capillaries;

FIGS. 6*a* and 6*b* illustrate two possible variants for mounting the capillaries;

FIGS. 7*a* and 7*b* are two photographs illustrating the distribution of the excitation beam after it has traveled along the capillaries, depending on the index of the medium which surrounds the capillaries and through which said excitation beam travels;

FIG. 8 is a graph on which the response of the system has been plotted as a function of the concentration of fluorescein;

FIG. 9 is a graph on which the signal/noise ratio per capillary has been plotted;

FIG. 10 is a graph on which the signal/noise ratio has been plotted as a function of the power of the laser, for three different fluorescein concentrations;

FIG. 11 is a graph on which the intensity of the signal/noise ratio has been plotted as a function of the aperture of the objective;

FIG. 12*a* is a graph on which the collected intensity has been plotted as a function of time for a specimen separation example used with the system illustrated in FIG. 1;

FIG. 12*b* is a graph on which the collected intensity has been plotted as a function of time for a DNA separation example used with the system illustrated in FIG. 1.

FIGS. 13–17 illustrate various possible embodiments of the invention.

Figure 18:
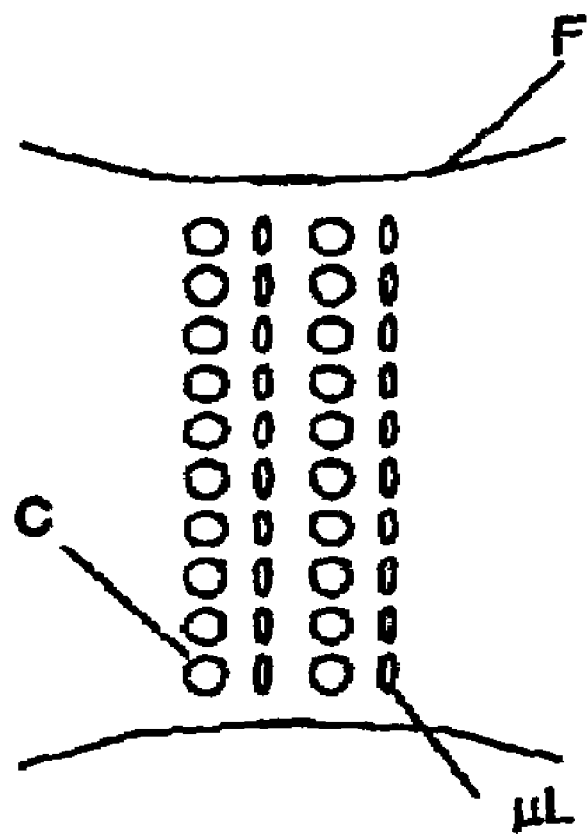

FIG. 18 illustrates the use of a matrix of capillaries and microlenses.

Figure 19:
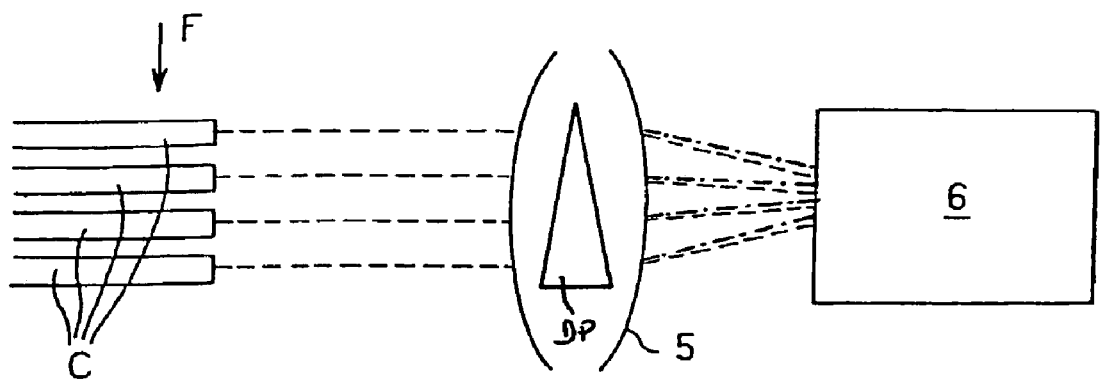

FIG. 19 illustrates an embodiment including prism dispersion means.

Figure 20:
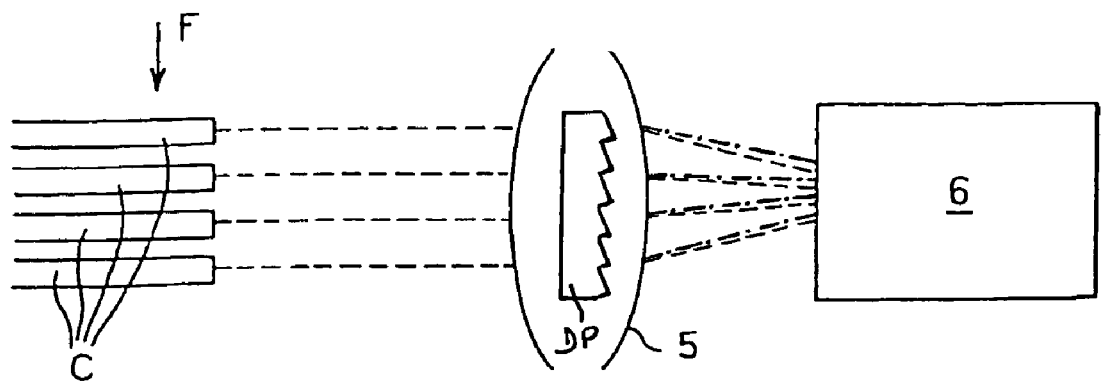

FIG. 20 illustrates an embodiment including diffraction grating dispersion means.

Figure 21:
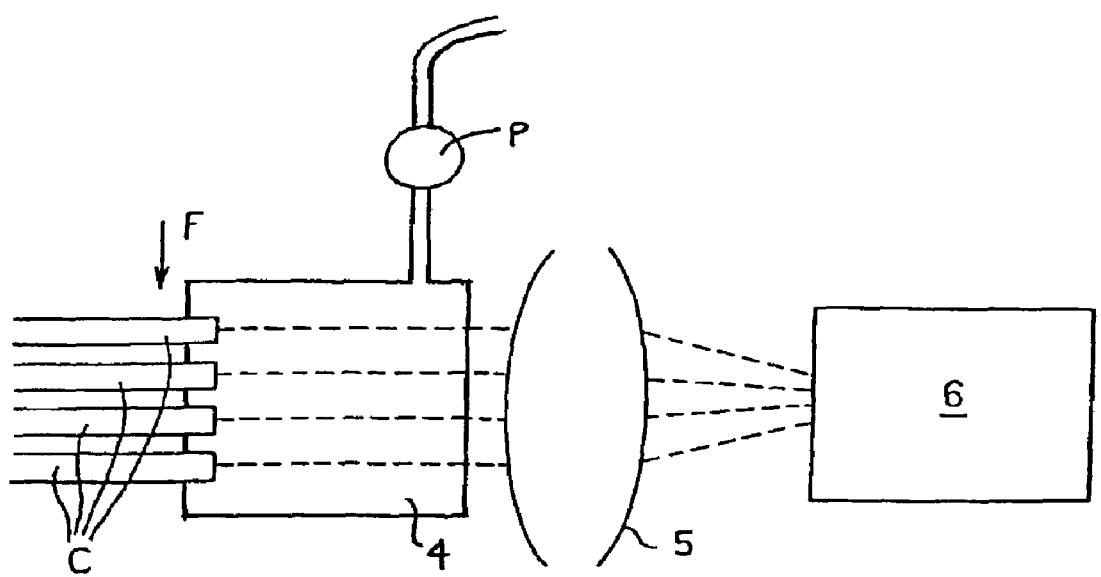

FIG. 21 illustrates an embodiment having a pump coupled to a detection cuvette to apply pressure in the cuvette.

The multicapillary electrophoresis system shown in FIG. 1 comprises, on an optical table 1:

a channel 3 along which the capillaries extend;

a high-voltage box 2 with heating, on which box the capillary entries are mounted and into which a temperature control system is integrated;

a detection cell 4 placed at the exit of the channel 3;

a CCD camera 6 and a convergence optic 5 which are interposed between said camera 6 and the detection cell;

a laser source 7;

optical means 8 which are mounted on a rail 9 and which allow the beam from the source 7 to be directed onto the detection cell 4.

Figure 2:
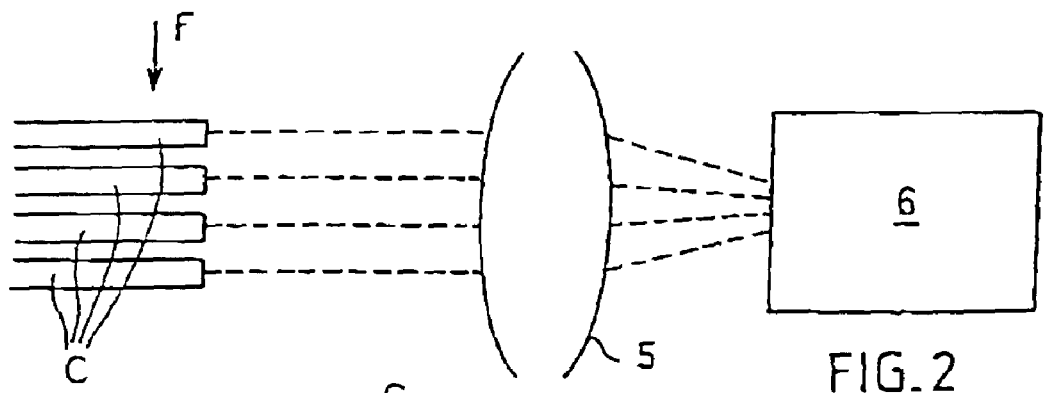
FIG. 2 is a schematic representation illustrating the arrangement of the detection means with respect to the capillaries for the system of FIG. 1.

As is more particularly illustrated in FIG. 2, the CCD camera 6 observes the fluorescence of the molecules excited inside the capillaries by the laser beam F along an optical axis which is parallel to the axis of the capillaries C. The CCD camera 6 collects the fluorescence light coming directly from the excited molecules, which light forms a cone around the axis of said capillary over the solid angle between the position of the excited molecules in the capillary and the opening of said capillary.

As long as the resolution of the camera is high enough, this allows the light emerging from the inside of the capillaries C to be distinguished from that coming from the walls of the latter and/or from the medium which surrounds them. As a result, the signal-to-noise ratio is considerably improved.

For example, in the case of capillaries C having an internal diameter of 100 µm and an external diameter of 300 µm, it is possible to use, as detector, a CCD camera 6 providing, in combination with the optical means 5, a resolution of the order of 20 µm.

In addition, to minimize the background noise coming from the scattering of the laser beam F or the fluorescence of the walls of the capillaries C or the surrounding medium, a black mask forming a diaphragm is advantageously mounted at the exit of the capillaries C.

It will be noted, given that the fluorescence of the molecules is observed at the exit of the capillaries C along an axis parallel to the direction of the capillaries C, it becomes possible to use matrices of capillaries C, thereby allowing the electrophoresis efficiency to be considerably increased. The term matrix should be understood in a general manner and it denotes any assembly of capillaries C in which the latter are distributed in a superposed fashion with respect to one another in two directions. This term consequently encompasses matrices consisting of several superposed linear arrays just as well as other arrangements of capillaries and especially, for example, assemblies in which the capillaries are distributed in a staggered fashion.

The number of capillaries per matrix may vary greatly. Tests have been carried out on matrices of 16, 50 and 100 capillaries. A greater number of capillaries per matrix could also be envisioned.

The excitation beam F emitted by the laser source 7 is sent onto the detection cell 4, in order to strike the capillaries C perpendicular to the direction along which they extend.

The excitation beam F may then be either circular in cross section (FIGS. 3*a* and 3*b*), in which case it is sent in the plane of a linear array of capillaries C in order to pass in succession through the latter.

Also advantageously, it may be elongate (for example elliptical) and strike a linear array in an optical direction perpendicular to the plane of said linear array, thereby allowing the same beam F to strike the various superposed capillaries C simultaneously (FIGS. 4*a* and 4*b*). Furthermore, this allows a greater tolerance on the relative position of the capillaries.

In addition, as illustrated in FIG. 5, it will be advantageous to use an elliptical beam F when the capillaries C are distributed not in a linear array but in a matrix.

The capillaries C may be held together by bonding and/or by performs.

Moreover, as illustrated in FIG. 6a, it is possible to provide, along the path of the excitation beam, in the interstices between the capillaries C, a material whose refractive index is chosen so that the excitation beam does not diverge after having been crossed by a capillary, especially a material whose index is less than that of the capillaries.

This material is also chosen to be as transparent as possible and non-fluorescent.

The focusing effect obtained with such a material is illustrated by the photographs given in FIGS. 7a and 7b. It may be seen in these photographs that a beam F illuminating several capillaries C in parallel creates shadow regions after passing through the capillaries C when the indices of the capillaries C and of the surrounding medium are similar, but that the light transmitted is focused when the external index is less than that of the capillaries C. Thus, the light at the exit of each of the capillaries is focused onto the capillary of the next row, which is directly opposite.

This multiple focusing makes it possible, for example, to use the same elliptical beam F to illuminate various rows of capillaries C.

This focusing effect also allows the laser beam to be used in an advantageous manner. Almost all of its intensity is focused in the various capillaries.

Such focusing can be achieved using an array of capillaries or else more perfectly by microlenses. This focusing decreases the power of the laser necessary by at least a factor of 3, creating at the same time less noise.

The material which provides the focusing function may optionally consist of the material which serves for fixing the capillaries. However, it is preferred to use the solutions in which, in order to prevent divergence of the excitation beam which crosses the capillaries, a material different from that used for fixing the capillaries.

Moreover, as illustrated in FIG. 7b, it will be noted that in this case the material which prevents the divergence of the excitation beam may consist of the buffer solution bathing the capillaries.

Technical details are given below relating to the set-up illustrated in FIG. 1, which was used by the inventors.

The electrode in the box 2 is supplied by a voltage generator sold by the company SPELLMAN.

The entries and exits of the capillaries C are electrically connected via a buffer or a polymer solution to the cathode and to the anode of this generator.

The voltage applied to the cathode may range up to 30 kV for a length of capillaries C of between 15 and 60 cm, the anode being at earth potential.

The detection cell 4 from which the capillaries C emerge is a rectangular parallelepiped with opaque walls, provided with two lateral quartz windows for the entry and exit of the laser beam F, while another window, also made of quartz, lies on the axis of the capillaries C in order to allow the fluorescence light to be collected by the optic 5 and the camera 6.

This latter window may be replaced with a filter in order for the fluorescence light to be discriminated from the laser light. As a variant, this filter may be placed at the exit of said window.

A fourth window, in the upper wall of the cell allows the alignment of the laser beam F with respect to the capillaries C to be observed.

The adhesive used for fixing the capillaries C in the detection cell is a transparent UV-curable adhesive.

The optic 5 is an objective which has a focal length of 1.2 [lacuna]. It is advantageously completed by two auxiliary lenses with a total of six diopters, in order to obtain a magnification close to 1.

Alternatively, the optic 5 may consist of two objectives, the first of which is inverted. A multicolor dispersion system is advantageously mounted between the two objectives.

Also as a variant, the optic 5 may advantageously incorporate a fiber-optic bundle interposed between the exits of the capillaries and the CCD camera.

The CCD camera 6 is of the type of those sold by PRINCETON under the name "frame transfer". It allows successive acquisitions to be made without dead time and without a mechanical shutter.

The active area of the camera is 6 to 8 mm$^2$ with a pixel size of 22 µm/22 µm.

The camera is cooled down to approximately −40° C. by the Peltier effect.

The laser is an argon laser (from ILT) having a maximum power of approximately 100 mW at a wavelength of 488 nm.

A holographic prism allows any wavelength other than this 488 nm wavelength to be eliminated.

The separating matrix (a gel or other material) is injected into the capillaries by means of a pump which allows pressure to be applied in the detection cuvette. FIG. 21 illustrates a pump (P) coupled to detection cuvette 4 to apply pressure in the cuvette.

Presented below are the results which were obtained with such a system, for a power of 40 mW of the laser beam F and a distance of 750 µm between the exit faces of the capillaries C and the point of impact of the detection excitation beam F, by injecting, electrokinetically or with a hydrodynamic flow, dilutions of oligonucleotides of a known concentration.

FIG. 8 gives the number of charges collected on 25 pixels (summation by the software) as a function of the concentration of fluorescein sulfate injected. Good linearity is observed in the region shown, which has been checked between 0.05 and 100 nmol/l. The two straight lines correspond to the charges collected for a central capillary and one at the edge of the row, respectively. The difference is explained by the Gaussian distribution of the laser beam (conventionally elliptical).

With regard to the minimum detectable sensitivity, FIG. 9 gives the signal/noise (S/N) ratio as a function of the capillary number, obtained for a concentration of 1 nmol/l of fluorescein. A signal/noise ratio of greater than 50 is observed. Even seen from the edge, this ratio is broadly satisfactory for sequencing or genotyping experiments.

In order to improve the sensitivity further, larger pixels may be used, for example by grouping together the 25 pixels previously envisioned. In this case, a sensitivity of approximately three—five times higher—is obtained. This arises from the fact that the read noise of the camera is almost 25 times higher if 25 pixels are read individually than when they are grouped together into a single pixel.

As may be observed in FIG. 10, it is also possible to gain in sensitivity by simply increasing the power of the laser. This shows that the system is not at its limit.

The dependence of the gathered light on the aperture of the objective was also tested. The signal/noise ratio is given for three different apertures of the objective in FIG. 11.

Moreover, the tests carried out by the inventors have shown that the sensitivity of the system also depended on the position of the point of impact of the laser with respect to the exit of the capillaries C. However, the latter varies little when the distance between said point of impact and the exit is varied from 2 mm to 250 µm, thereby confirming that essentially all the light exiting the opening of the capillaries C is effectively collected. In order to increase the sensitivity further, it would therefore be necessary for the beam F to be considerably closer to the exit of the capillaries C. Such a gain would entail poorer collimation of the light, which would in turn partially degrade the resolution of the image.

In order to demonstrate the capability of the system to separate the bands, the inventors carried out a migration test on the double-strand specimen (φ X174 from Gibco BRL) in a polymer solution (0.5% HPC) The marker used was the SYBR(I) insert (from Molecular Probes). The result is plotted on the graph in FIG. 12a for two capillaries C. For a concentration of 1 ng/μl, the inventors obtained good separation of the bands and a good signal-to-noise ratio.

The inventors also carried out separation tests on a DNA specimen (M13) of a sequence reaction (T-terminator kit from AMERSHAM, primer labeled with FITC from PHARMACIA) in a polymer solution (5% TIS from the CURIE INSTITUTE) at 55° C. (FIG. 12b). The figure illustrates the quality of separation, the good signal-to-noise ratio and the separation rate (600 bases in 1 h).

Further aspects of possible embodiments of the invention will now be described.

In one embodiment, the liquid medium Mee which is surrounding the capillaries presents a refractive index which is equal or superior to that of the liquid medium Mei inside the capillaries. This characteristic increases light transmission through the walls and limits multiple reflections. As illustrated on FIG. 13, because of this index difference, light transmitted through the walls of the capillaries is strongly deflected, which allows—in combination with an appropriate optical resolution—to discriminate light transmitted through the walls from light directly emitted by DNA molecules For example the outside Mee and inside Mei media have a refractive index of 1.35 whereas the capillaries walls—which are made out of glass—have a refractive index of 1.5.

In another embodiment of the invention, the medium Mee outside of the capillaries presents a refractive index lower than that of the medium Mei inside of the capillaries. In such a case, the outside of the walls of the capillaries is advantageously turned black between the excitation beam and the end of the capillaries so that this black part of the walls will absorb light instead of reflecting it.

Figure 14A:
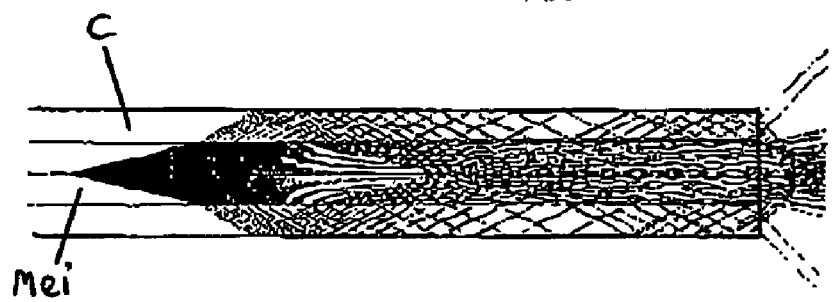
Figure 14B:
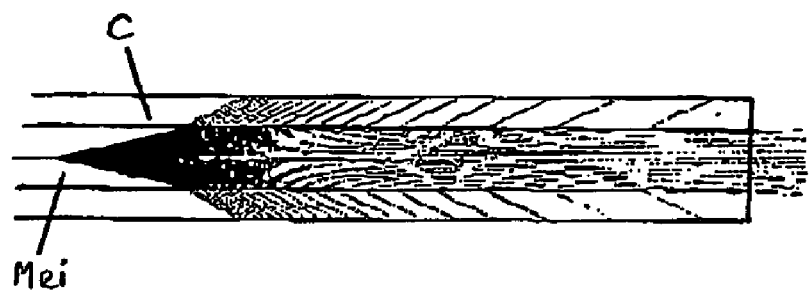

This embodiment allows to reduce considerably the noise by eliminating all light trajectories other than those emerging from fluorescent molecules inside the capillaries. The advantage of this system is that it does not require means for discriminating noise from the signal. FIG. 14a shows the beams reflecting on the capillary walls and FIG. 14b shows the beams in the case the walls are blackened.

Figure 15:
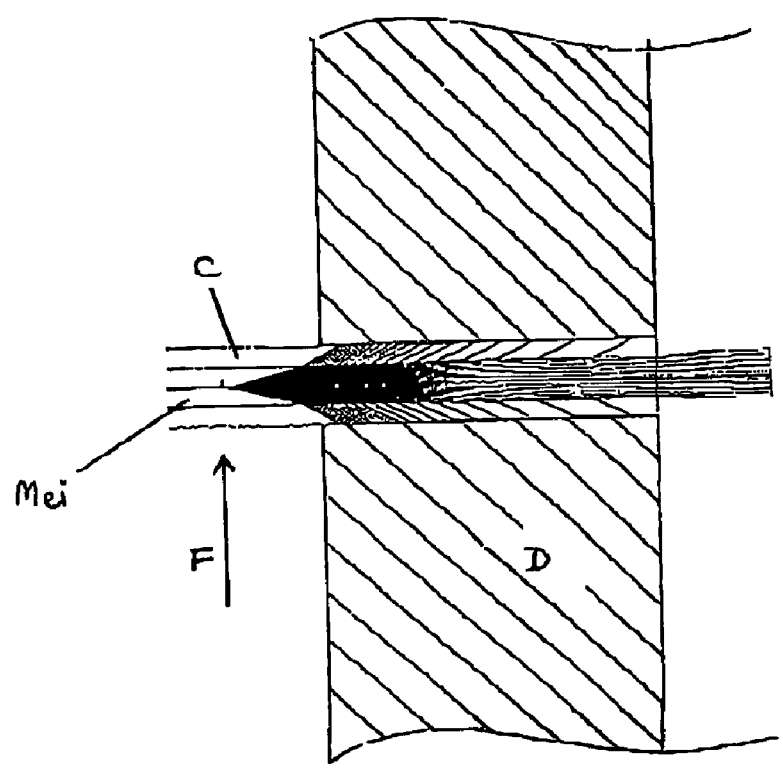
Figure 16A:
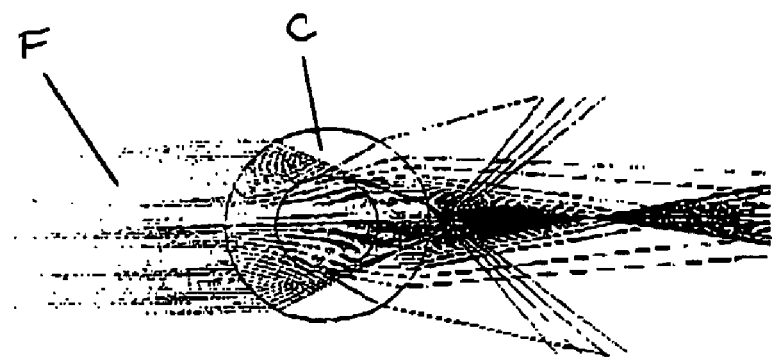
Figure 16B:
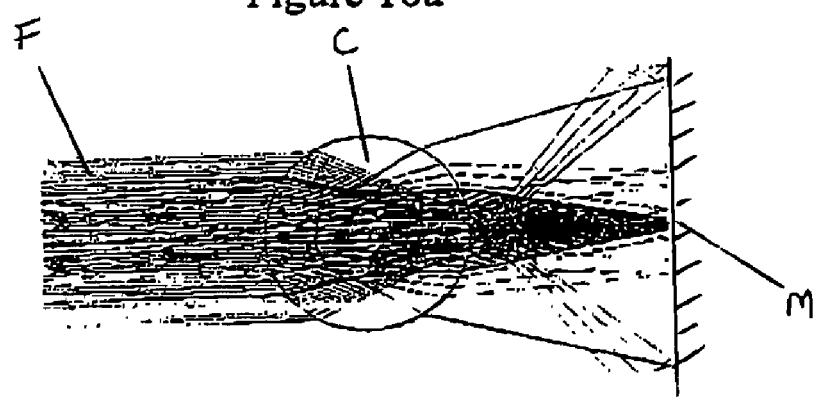
Figure 16C:
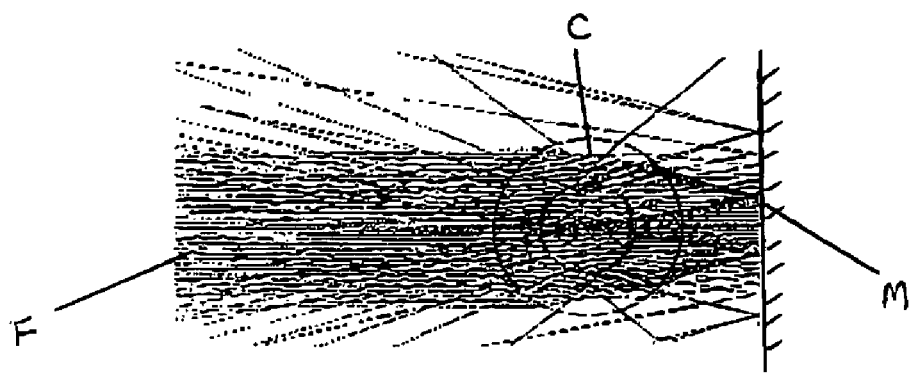
Figure 16D:
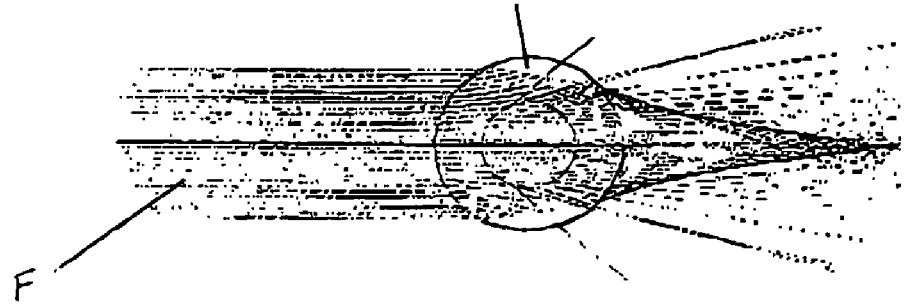

As one can see on FIG. 15, the blackening of the walls can advantageously be achieved by gluing the capillaries C on their support with non transparent glue, preferently dark glue, such support consisting of the detection cell wall D.

In addition to noise reduction, this arrangement allows not to deal anymore with bubbles which could appear between the capillaries, considering that the laser light does not cross the buffer solution or the cell polymer, that way avoiding to produce spurious fluorescence.

Figure 17:
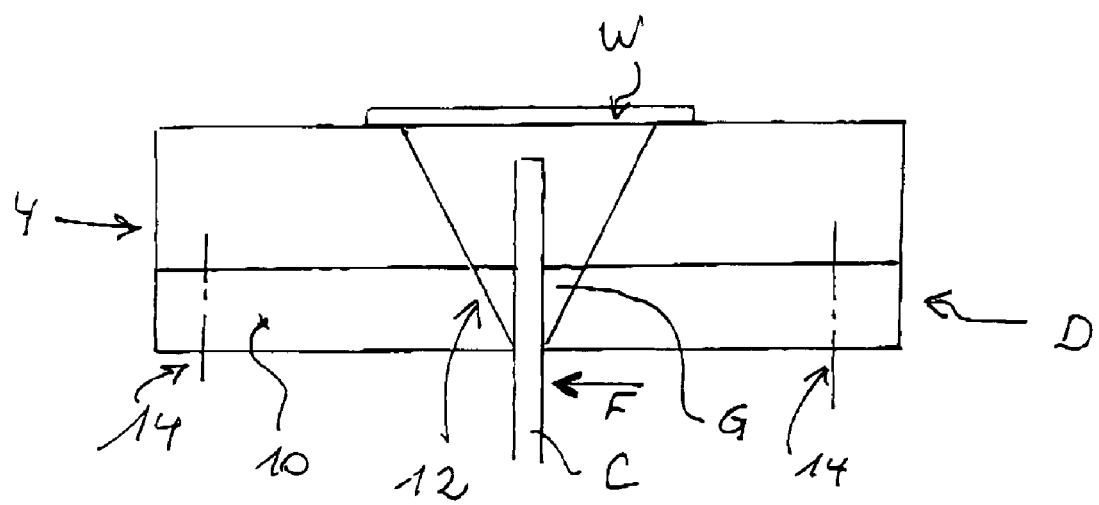

FIG. 17 illustrates an embodiment wherein the array of capillaries C is fixed by glue on a support D made of a plate 10. Typically the plate 10 has a thickness about 2 mm. More precisely the plate 10 includes an array of bores 12 each receiving a respective capillary C. The plate 10 is fixed by any means 14 on the detection cell 4 having a window W in regard of the end of the capillaries C. According to the preferred embodiment each bore 12 is flared towards the inside of the cell 4 in a conical shape. The conical shape of the bore receiving the glue G is preferred so that said glue G resists the internal pressure of the cell 4. As indicated above the glue G is not transparent so as to absorb the beams instead of reflecting them. On FIG. 14 the place of impacting the laser beam is schematically illustrated under F.

When suitable the plate 10 with the glued array of capillaries may be removed from the cell 4 and replaced.

In another embodiment of the invention, a mirror M is facing the laser source on the side of the capillaries C which is opposed to the laser source (said capillaries being interposed between laser source and said mirror). The mirror receives the laser beam which has gone through the capillaries and reflects it, making the laser beam pass twice through the capillaries and consequently increasing the laser efficiency.

This embodiment moreover has the advantage of minimising the laser intensity in the walls and to improve the signal to noise ratio. As one can see on FIGS. 16a to 16d, this device multiplies the light intensity in the capillaries more than twice. Since capillaries C are behaving like lenses and are focusing light, the beam can be focussed inside the matrix external capillaries providing that the mirror M be correctly placed. This embodiment allows to further intensify the flux F of photons crossing the path of the migrating DNA and to limit the quantity of photon crossing the capillary walls.

Further, the distance between the end of the capillaries and the impact of the laser beam on the capillaries is advantageously chosen between 6 and 30 times the internal diameter of the capillaries, which corresponds to a longer of 5 to 1° for the fluorescence light coming out of the capillaries.

Of course, variants other than the one just described may be envisioned. In particular, the fluorescence light beams exiting the capillaries C—which are collimated—may be directly transmitted to one or more intermediate prisms or else to a diffraction grating in order to spatially separate the various wavelengths emitted and to separate them on an array of photodetectors.

FIG. 18 illustrates the use of a matrix of capillaries and microlenses μL.

FIG. 19 illustrates the embodiment illustrated in Figure with the addition of dispersion means in the form of a prism.

FIG. 20 illustrates the embodiment illustrated in Figure with the addition of dispersion means in the form of diffraction grating.

As will have been understood, the systems that have just been described are simple in design and allow high throughput to be achieved with great reliability and great ease of implementation.

What is claimed is:

1. Multicapillary electrophoresis system comprising a plurality of juxtaposed capillaries, at least one source configured for the emission of a light beam intended to excite molecules lying in its path and inside the capillaries and means for detecting the fluorescence of the molecules excited by said light beam, wherein said means are arranged so as to detect light which emerges at the exit of said capillaries and which propagates along the direction in which said capillaries extend, the resolution of the detection means is high enough to distinguish light which emerges at the exit of each of the capillaries, a first liquid is disposed outside of the capillaries, and a second liquid is disposed inside of the capillaries, the first liquid has a first refractive index and the second liquid has a second refractive index, wherein said first refractive index is equal to or superior to said second refractive index, and a mirror is facing the at least one source on the side of the capillaries which is opposed to said source.

2. The multicapillary electrophoresis system according to claim 1, wherein the resolution of the detection means is high enough to distinguish the light which emerges at the exit of each of the capillaries from that coming from walls of the capillaries and/or from a liquid medium which surrounds the capillaries.

3. The multicapillary electrophoresis system according to claim 1, said plurality of juxtaposed capillaries forming at least one linear array.

4. The multicapillary electrophoresis system according to claim 3, further including means for producing multiple focusing for the light beam on the at least one linear array.

5. The multicapillary electrophoresis system according to claim 4, wherein said second liquid is transparent and non-fluorescent.

6. The multicapillary electrophoresis system according to claim 4, wherein said means for producing multiple focusing of the light beam on the at least one linear array of capillaries comprises microlenses positioned juxtaposed to the at least one linear array of capillaries.

7. The multicapillary electrophoresis system according to claim 3, wherein the light beam exiting a side of one capillary of the at least one linear array of capillaries is focused onto an adjacent juxtaposed capillary within another linear array of capillaries following the at least one linear array of capillaries.

8. The multicapillary electrophoresis system according to claim 7, wherein a space between the capillaries is filled, at least along the path of the excitation beam, with the first liquid, wherein the first refractive index is chosen so that the light beam does not diverge after having traveled through a capillary.

9. The multicapillary electrophoresis system according to claim 1, wherein the light beam is of elongate cross section and strikes several juxtaposed capillaries simultaneously.

10. The multicapillary electrophoresis system according to claim 1, wherein the detection means provide a complete image of the light exiting the capillaries.

11. The multicapillary electrophoresis system according to claim 1, wherein the detection means is a charge-coupled device (CCD) having beam focusing capability.

12. The multicapillary electrophoresis system according to claim 1, wherein the detection means is a charge-coupled device (CCD) and a fiber bundle interposed between the exits of the capillaries and the CCD.

13. The multicapillary electrophoresis system according to claim 1 wherein the portion of the outside of the wall of the capillaries between the impact of the excitation beam and the end of the capillaries is blackened.

14. The multicapillary electrophoresis system according to claim 13 wherein the capillaries are glued on a support.

15. The multicapillary electrophoresis system according to claim 14, wherein the capillaries are glued on the support using a non transparent glue.

16. The multicapillary electrophoresis system according to claim 1, wherein the capillaries are fixed on a support with glue and one end of the capillaries is disposed in a cell under pressure, said glue suitable to resist the internal pressure of the cell.

17. The multicapillary electrophoresis system according to claim 1, wherein the distance between the impact of the excitation beam on the capillaries and the end of the capillaries is between 6 to 30 times the internal diameter of the capillaries.

18. A multicapillary electrophoresis system comprising:
a plurality of juxtaposed capillaries each having an entrance and an exit,
at least one source configured for the emission of a light beam intended to excite molecules lying in its path and inside the plurality of juxtaposed capillaries and means for detecting the fluorescence of the molecules excited by said light beam, wherein said means are arranged so as to detect light which emerges at the exit of said plurality of juxtaposed capillaries and which propagates along a direction in which said plurality of juxtaposed capillaries extend, the resolution of the detection means is high enough to distinguish the light which emerges at the exit of each of the plurality of juxtaposed capillaries, and a portion of the outside of a wall of the capillaries between the impact of the excitation light beam and the exit of the capillaries extending to the end of the capillaries is blackened.

19. The multicapillary electrophoresis system according to claim 18, wherein the resolution of the detection means is high enough to distinguish the light which emerges at the exit of each of the plurality of juxtaposed capillaries from that coming from walls of the latter and/or from a first liquid which surrounds the plurality of juxtaposed capillaries.

20. The system according to claim 18, further including said plurality of juxtaposed capillaries forming at least one linear array.

21. The system according to claim 20, further including means for producing multiple focusing of the light beam on a linear array of capillaries.

22. The system according to claim 21, wherein said means for producing multiple focusing of the light beam on a linear array of capillaries comprises microlenses positioned juxtaposed to the linear array of capillaries.

23. The system according to claim 20, wherein the beam exiting a side of one capillary of one linear array is focused onto an adjacent juxtaposed capillary within a following linear array.

24. The system according to claim 23, further including a space between the capillaries of the plurality of juxtaposed capillaries is filled, at least along the path of the excitation beam, with a liquid whose refractive index is chosen so that the excitation light beam does not diverge after having traveled through a capillary of the plurality of juxtaposed capillaries.

25. The system according to claim 24, wherein said liquid is transparent and non-fluorescent.

26. The system according to claim 18, wherein the excitation light beam is of elongate cross section and strikes several juxtaposed capillaries simultaneously.

27. The system according to claim 18, wherein the detection means provide a complete image of the light exiting the plurality of juxtaposed capillaries.

28. The system according to claim 18, wherein the detection means is a charge-coupled device (CCD) with focusing capability.

29. The system according to claim 18, wherein the detection means is a charge-coupled device (CCD) and a fiber bundle interposed between the exits of the capillaries of the plurality of juxtaposed capillaries and the CCD.

30. The system according to claim 18, wherein a first refractive index of a first liquid outside of the of the plurality of juxtaposed capillaries is less than that of a second liquid inside of the of the plurality of juxtaposed capillaries.

31. The system according to claim 18, further including the plurality of juxtaposed capillaries are glued on a support using a non-transparent glue.

32. The system according to claim 18, wherein the distance between the impact of the excitation light beam on the plurality of juxtaposed capillaries and the exit of the plurality of juxtaposed capillaries is between 6 to 30 times the internal diameter of each of the capillaries of the plurality of juxtaposed capillaries.

33. The system according to claim 18, wherein a mirror is facing the at least one source on the side of the capillaries which is opposed to said source.

\* \* \* \* \*